United States Patent
Elsheikh et al.

(10) Patent No.: US 6,528,691 B1
(45) Date of Patent: *Mar. 4, 2003

(54) PREPARATION OF 245FA

(75) Inventors: Maher Y. Elsheikh, Tredyffrin, PA (US); Bin Chen, Tredyffrin, PA (US)

(73) Assignee: Atofina Chemicals, Inc., Philadelphia, PA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 44 days.

(21) Appl. No.: 09/312,267

(22) Filed: May 14, 1999

(51) Int. Cl.[7] ................................ C07C 17/08

(52) U.S. Cl. ........................................ 570/167
(58) Field of Search ......................... 570/167

(56) References Cited

U.S. PATENT DOCUMENTS 5,616,819 A * 4/1997 Boyce et al. ............... 570/167

FOREIGN PATENT DOCUMENTS

WO    WO97/24307    7/1997

* cited by examiner

*Primary Examiner*—Alan Siegel
(74) *Attorney, Agent, or Firm*—William D. Mitchell

(57) ABSTRACT

A gas phase process for the preparation of 245fa is provided, wherein 1233zd is contacted with HF in the presence of a supported antimony catalyst.

3 Claims, No Drawings

PREPARATION OF 245FA

BACKGROUND OF THE INVENTION

This invention relates to the preparation of 1,1,1,3,3-pentafluoropropane ("245fa") from 1,1,1-trifluoro-3-chloro-2-propene ("1233zd"), particularly to gas phase processes wherein said 1233zd is contacted with hydrogen fluoride ("HF") in the presence of a supported antimony catalyst. 1,1,1,3,3-Pentafluoropropane is known to have utility as a foam blowing agent and refrigerant.

WO 97/24307 discloses a gas phase process for the conversion of 1233zd to 245fa via reaction with HF in the presence of a chrome catalyst, but does not achieve high conversions of the 1233zd (generally at or below about 80%) so that a major portion of the desired 245fa product becomes azeotroped with the unreacted 1233zd, causing product loss and/or major separation problems. A process is therefore needed which permits high conversions of the 1233zd starting material.

BRIEF SUMMARY OF THE INVENTION

A gas phase process for preparing readily recoverable 245fa is provided, which process comprises (a) contacting 1233zd with HF in the presence of a supported antimony halide catalyst (preferably antimony fluoride); and (b) recovering 245fa from the resulting reaction mixture.

DETAILED DESCRIPTION

It has now been discovered that the use of a supported antimony catalyst in the gas phase hydrofluorination of 1233zd permits high conversions of 1233zd to 245fa, typically on the order of 95% or more, with 99–100% selectivity for 245fa, so that product loss is minimized or avoided altogether. In addition to 245fa, the resulting reaction mixture also contains coproduct hydrogen chloride (HCl), together with unreacted HF and 1233zd.

The 1233zd starting material can be prepared by known processes, such as fluorination of 1,1,3,3-tetrachloro-2-propene ("1230za") as taught in U.S. Pat. No. 5,616,819.

The HF:1233zd molar ratio is typically from about 0.5:1 to about 10:1, but is preferably from about 5:1 to 10:1. Temperatures of from about 110° C. to about 150° C. are typically used. Pressures are typically from about 0 to about 315 psig, preferably from about 115–170 psig. The contact time (total flow rate divided by the catalyst volume) is typically from about 1 to about 100 seconds, more typically from about 20 to about 60 seconds.

A supported antimony halide catalyst is used, the support typically being activated carbon, HF-treated activated carbon, graphite, fluorided graphite, alumina or fluorided alumina and the halide typically being chloride or, preferably, fluoride. The catalyst is typically prepared by adding an antimony V salt, such as antimony chloride, $SbCl_5$ to the support, loading the catalyst to a fixed bed reactor and activating the catalyst by feeding HF over the bed at about 50° C., resulting in conversion of the antimony chloride to antimony fluoride.

The HCl and HF can be separated from the resulting reaction mixture by conventional means. For example, the HCl can be distilled from the other compounds and the HF separated by scrubbing with water, metal fluoride adsorption, membrane separation or swing distillation. Metal fluoride adsorption can be conveniently out using an alkali metal fluoride such as KF or NaF to convert the HF to a metal fluoride.

A minor amount of the 245fa product will be azeotroped with unreacted 1233zd. However, since only a low level of 1233zd will be present, photochlorination can be used to convert the 1233zd to the high boiling 1,1,1-trifluoro-2,3,3-trichloropropane (b.p., 106° C.), which latter compound can be readily separated from the low boiling 245fa (b.p., 15° C.) by distillation.

The practice of the invention is illustrated in more detail in the following non-limiting examples.

EXAMPLE 1

Preparation of Antimony Halide Catalyst

Antimony (V) chloride was added to activated carbon, loaded to a fixed bed reactor, and activated with HF at 50° C.

EXAMPLE 2

Preparation of 245fa

A gas phase mixture of HF and 1233zd (molar ratio of 7.2:1) was fed over the catalyst bed of Example 1 at a temperature of 112° C. and a pressure of 151 psig for a contact time of 47 seconds, resulting in 96.6% conversion of the 1233zd, with selectivity of 99.7% for 245fa.

What is claimed is:

1. A gas phase process for preparing readily recoverable 1,1,1,3,3-pentafluoropropane which comprises (a) contacting 1,1,1-trifluoro-3-chloro-2-propene with hydrogen fluoride in the presence of a supported antimony halide catalyst under conditions sufficient to achieve at least about 95% conversion of said 1,1,1-trifluoro-3-chloro-2-propene; and (b) recovering 1,1,1,3,3-pentafluoropropane from the resulting reaction mixture.

2. A process as in claim 1 wherein the catalyst is a supported antimony fluoride catalyst.

3. A process as in claim 1 wherein unreacted 1,1,1-trifluoro-3-chloro-2-propene in the resulting reaction mixture from step (a) is photochlorinated prior to recovery of the 1,1,1,3,3-pentafluoropropane.

* * * * *